United States Patent
Von Blumenthal

(10) Patent No.: US 10,926,048 B2
(45) Date of Patent: Feb. 23, 2021

(54) MEDICAL SYSTEM WITH IMPROVED SECURITY DURING AN INTERACTION OF A MEDICAL MEASURING SYSTEM WITH A VENTILATOR OR ANESTHESIA DEVICE VIA A DATA NETWORK

(71) Applicant: Drägerwerk AG & Co. KGaA, Lübeck (DE)

(72) Inventor: Tilman Von Blumenthal, Lübeck (DE)

(73) Assignee: DRÄGER WERK AG & CO. KGAA, Lübeck (DE)

(*) Notice: Subject to any disclaimer, the term of this patent is extended or adjusted under 35 U.S.C. 154(b) by 329 days.

(21) Appl. No.: 15/927,306

(22) Filed: Mar. 21, 2018

(65) Prior Publication Data

US 2018/0272087 A1    Sep. 27, 2018

(30) Foreign Application Priority Data

Mar. 23, 2017  (DE) .................. 10 2017 002 775.7

(51) Int. Cl.
| | | |
|---|---|---|
| *A61M 16/00* | (2006.01) | |
| *A61M 16/10* | (2006.01) | |
| *G16H 20/10* | (2018.01) | |
| *G06F 21/60* | (2013.01) | |
| *G06F 21/62* | (2013.01) | |

(Continued)

(52) U.S. Cl.
CPC ...... *A61M 16/022* (2017.08); *A61M 16/0003* (2014.02); *A61M 16/0051* (2013.01);
(Continued)

(58) Field of Classification Search
CPC ........ A61M 16/00–026; A61M 16/104; A61M 16/0003; A61M 16/0051; A61M 2205/3592; A61M 2205/18; A61M 2205/3569; A61M 2205/3561; A61M 2205/6018; A61M 2230/432;
(Continued)

(56) References Cited

U.S. PATENT DOCUMENTS

| | | |
|---|---|---|
| 8,528,552 B2 | 9/2013 | von Blumenthal |
| 9,254,368 B2 | 2/2016 | von Blumenthal et al. |

(Continued)

OTHER PUBLICATIONS

IEEE, Transactions on Information Theory, vol. 22, No. 6, 1976, pp. 644-654.

(Continued)

*Primary Examiner* — Victoria Murphy
*Assistant Examiner* — Elliot S Ruddie
(74) *Attorney, Agent, or Firm* — McGlew and Tuttle, P.C.

(57) ABSTRACT

With the interaction of a medical measuring system (3) with a ventilator or anesthesia device (5) via a data network (60), data transmission security and mutual authentication between the medical measuring system (3) and the ventilator or anesthesia device (5) is improved in a medical system (1) by the use of asymmetric encryption pairs. A classification of the measuring systems (3) is possible on the basis of an identification/authentication provided by the asymmetric encryption pairs. The classification may be used to adapt a ventilation by the ventilator or anesthesia device (5) in respect to different defined measuring systems (3), for example, measuring systems (3) for detecting an oxygen saturation ($SpO_2$).

18 Claims, 5 Drawing Sheets

(51) Int. Cl.
    *H04L 9/32* (2006.01)
    *G16H 40/67* (2018.01)
    *G06F 21/44* (2013.01)
    *A61M 16/01* (2006.01)
    *G16H 20/40* (2018.01)

(52) U.S. Cl.
    CPC .......... *A61M 16/01* (2013.01); *A61M 16/024* (2017.08); *A61M 16/104* (2013.01); *G06F 21/445* (2013.01); *G06F 21/606* (2013.01); *G06F 21/6245* (2013.01); *G16H 20/10* (2018.01); *G16H 20/40* (2018.01); *G16H 40/67* (2018.01); *H04L 9/3247* (2013.01); A61M 2016/103 (2013.01); A61M 2202/0208 (2013.01); A61M 2205/18 (2013.01); A61M 2205/3561 (2013.01); A61M 2205/3569 (2013.01); A61M 2205/3584 (2013.01); A61M 2205/3592 (2013.01); A61M 2205/6018 (2013.01); A61M 2230/205 (2013.01); A61M 2230/432 (2013.01); H04L 2209/805 (2013.01); H04L 2209/88 (2013.01)

(58) Field of Classification Search
    CPC .... A61M 2205/3584; A61M 2230/205; A61M 2202/0208; A61M 2016/103; G16H 10/00; G16H 20/00; G16H 20/40; G16H 40/67; G16H 20/10; G06F 21/44–445; G06F 21/6245; G06F 21/606; H04L 2209/88; H04L 2209/805
    See application file for complete search history.

(56) References Cited

U.S. PATENT DOCUMENTS

| | | |
|---|---|---|
| 2008/0000479 A1 | 1/2008 | Elaz et al. |
| 2008/0097913 A1 | 4/2008 | Dicks et al. |
| 2010/0299517 A1* | 11/2010 | Jukic ................ H04L 12/2809 713/150 |
| 2012/0232359 A1* | 9/2012 | Al-Ali ................ A61B 5/6838 600/301 |
| 2016/0321400 A1* | 11/2016 | Durrant ................ A61B 5/0402 |
| 2017/0068791 A1 | 3/2017 | Hermann et al. |

OTHER PUBLICATIONS

Public-key cryptography: https:llen.wikipedia.org/w/index. php?title=Public-key_ cryptography&oldid= 771039877.

* cited by examiner

MEDICAL SYSTEM WITH IMPROVED SECURITY DURING AN INTERACTION OF A MEDICAL MEASURING SYSTEM WITH A VENTILATOR OR ANESTHESIA DEVICE VIA A DATA NETWORK

CROSS REFERENCE TO RELATED APPLICATIONS

This application claims the benefit of priority under 35 U.S.C. § 119 of German Application 10 2017 002 775.7, filed Mar. 23, 2017, the entire contents of which are incorporated herein by reference.

FIELD OF THE INVENTION

The present invention pertains to medical systems and issues related to an interaction of a medical measuring system with a ventilator (also known as a respirator) or an anesthesia device via a data network.

BACKGROUND OF THE INVENTION

A patient, who is under medical care, treatment and therapy in a hospital, especially in an intensive care unit, is often connected to a plurality of medical devices, which are connected to one another partly via direct connection lines for the unidirectional and/or bidirectional data exchange via a data network (LAN, WLAN). Status data of the participating devices are available in this manner to other devices in this data network, and patient measured data detected at a device are likewise available to one or more other devices in the data network via the data network. Due to a combination of a physiological monitor, which measures an oxygen saturation ($SpO_2$) of a patient, for example, by means of a transmitted light sensor (finger clip sensor) placed on the finger of the patient or of a sensor placed on the ear, with a ventilator in the data network, the ventilator can provide expanded therapeutic possibilities.

For example, the ventilation of a patient by means of a ventilator can be carried out in this manner in a closed control loop with the oxygen saturation as an input variable as a so-called "$SpO_2$ closed loop ventilation," as it is described in U.S. Pat. No. 8,528,552 B2 and in U.S. Pat. No. 9,254,368 B2.

US 2008/000479 A1 describes a so-called "Patient Area Network" (PAN), via which the operation of a ventilator is carried out with the use of one or more hemodynamic parameters. The type of operation of the ventilator is adapted in this case as a function of the hemodynamic parameters. Hemodynamic parameters are, for example, blood pressure, temperature, $SpO_2$, and EKG.

SUMMARY OF THE INVENTION

Based on this state of the art, an object of the present invention is to improve the security in the interaction via a data network in a system with a medical measuring system and with ventilator or anesthesia device configured for the ventilation of a patient. The security shall be improved in the unidirectional data exchange, and especially also in the bidirectional data exchange between the medical measuring system and in the ventilator or anesthesia device.

The present invention pertains to a system, which is formed from a medical measuring system and a ventilator or anesthesia device.

The medical measuring system is configured especially as a physiological monitor, which is suitable for monitoring vital parameters of a living being, which is suitable for detecting and providing a plurality of physiological measured variables, especially heart rate (pulse), blood pressures (NIBP, IBP), oxygen saturations ($SpO_2$), carbon dioxide concentrations in the exhaled breathing gas ($etCO_2$) or electrocardiograms (EKG).

The basis of the present invention is to configure the medical system in terms of the type of data exchange in a data network, which is necessary for the interaction in the medical system between the measuring system and the ventilator or anesthesia device, such that the device that receives data from another device is enabled to identify a particular group of devices to which the device sending the data belongs. In particular, the ventilator or anesthesia device shall identify in this manner that the measuring system sending the data belongs to different groups of measuring systems. A device functionality of the ventilator or anesthesia device shall thereupon be adapted as a function of the belonging of the identified measuring system to a certain group of measuring systems by control or regulating elements of the ventilator or anesthesia device, which elements are suitable for such adaptations. A group of measuring systems may contain, for example, certain measuring systems, which are both configured for a continuous detection of measured values of an oxygen saturation ($SpO_2$) and for providing the measured values, and are configured concerning measuring properties such that ventilation of a patient in a closed control loop with the oxygen saturation as an input variable ("$SpO_2$ closed loop ventilation") is made possible on the basis of the measured values provided for a ventilator with measuring systems of this group of measuring systems.

Furthermore, the present invention also comprises the adaptation of the functionality of the measuring system on the basis of data received from the ventilator or anesthesia device. The ventilator or anesthesia device is identified in this case on the basis of the received data and the ventilator or anesthesia device is assigned on the basis of the identification to a certain ventilator or anesthesia device or to a certain group of ventilators or anesthesia devices.

An adaptation of the functionality is carried out on the measuring system by means of suitable control elements of the measuring system as a function of the assignment.

The identification of the measuring system (participant M1) at the ventilator or anesthesia device (participant B2) or of the ventilator or anesthesia device (B2) at the measuring system (M1) is carried out by means of an authentication, which is carried out in the data network on the basis of a method, which is especially suitable for this authentication and is known from cryptography, the so-called asymmetric encryption method (public key encryption method).

Some of the terms used within the framework of this patent application will be explained in more detail at the beginning.

A control signal is defined in the sense of the present invention as an individual control signal, a control signal as part of a set of control signals, as well as as a plurality or a set of control signals. An information signal is defined in the sense of the present invention as an individual information signal, an information signal as part of a set of information signals, as well as as a plurality or a set of information signals.

A sensor signal is defined in the sense of the present invention as a single sensor signal and/or a plurality of sensor signals, which are detected by the measuring system by measurement by means of sensors. They may be analog current or voltage signals, modulated signals (PCM, AM, FM) or digital signals generated by means of conversions and data processing (signal filtering, signal amplification) into data sets and/or data items. The sensor signals are, in particular, signals that indicate physical states, for example, temperatures, pressures, flow rates, concentrations or saturations of gases in fluids, partial pressures or other measured variables or variables derived from measured variables, which indicate physiological states of a patient.

A data set or a data item is defined in the sense of the present invention as an individual data set, a data set as part of a data item, as well as as a plurality or a set of data sets or data items.

An output signal is defined in the sense of the present invention as an individual output signal, an output signal as part of a set of output signals, as well as as a plurality or a set of output signals. An output signal may be configured as a preset value, set value, set point, setting value or operating parameter for influencing a manner of functioning of the medical system, the measuring system, especially the physiological monitor or the ventilator or anesthesia device.

A data link in a data network is defined in the sense of the present invention as a connection of at least two participants (M1, B2) by means of a wired, wireless or optical connection, which is suitable for transmitting output signals, control signals, data signals or output signals. Both direct physical connections (cable connections, wireless connections, light guide connections) as well as indirect or logic connections for transmitting information signals, control signals, data signals or output signals with physical or data technology-based conversions or transformations of signals, voltages, currents are covered. The data network is usually configured as a network (LAN, WLAN, Ethernet, Intranet, Internet), in which a packet-based data transmission takes place via a plurality of different possible physical transmission pathways (routing pathways) via a plurality of participating network nodes (routers), wherein the data transmission takes place in a protocol-based manner with Transmission Control Protocol (TCP, Transport Layer) and Internet Protocol (IP, Network Layer) according to a network data transmission protocol (TCP/IP protocol).

An asymmetric encryption is defined in the sense of the present invention as a type of data exchange of control signals, sensor signals, data signals, output signals between two participants (sender, receiver) in a data network, wherein an asymmetric encryption pair has a public key (ÖS) and a private key (PS). A known documented method is the so-called Diffie-Hellman Key Exchange (*IEEE, Transactions on Information Theory*, Vol. 22, No. 6, 1976, pp. 644-654). Asymmetric encryption systems are also known under the terms asymmetric crypto system, Rabin crypto system, Elgamal crypto system, RSA encryption method. Asymmetric crypto systems are based on so-called "trapdoor functions," i.e., functions that are easy to calculate but are practically impossible to invert without a secret. The public key is then a description of the function, and the private key is the "trapdoor." One prerequisite is, of course, that the private key cannot be calculated from the public one. In order for the crypto system to be able to be used, the public key must be known to the communication partner.

The decisive advantage of asymmetric methods is that they reduce the key distribution problem. Asymmetric encryption systems have the advantage over symmetrical methods that no eavesdropping-proof and/or manipulation-protected transmission pathway or channel is necessary before the data exchange proper is carried out. By contrast, a key must be exchanged in symmetrical methods via a secure, i.e., eavesdropping-proof and manipulation-protected channel before the use. Since the public key is not secret, the channel does not need to be eavesdropping-proof in case of asymmetric methods. The only thing that is necessary is that the public key is able to be assigned to the owner of the corresponding private secret key without any doubt. This is configured in practice such that, for example, a trustworthy certification office can issue a digital certificate, which assigns the public key to the private owner of the key. As an alternative to this, a web of trust may also be set up without a central office by the mutual certification of keys.

It is necessary for the security of asymmetric methods that the functions on which the different methods are based be practically irreversible as one-way functions, because the private, secret key could otherwise be calculated from the public key. So-called digital signatures are used during the data transmission to check the identity of the two participants (M1, B2) and to check the genuineness of the exchanged data. Asymmetric encryption is a cryptographic method for data exchange between the two participants (M1, B2), wherein each participant (M1, B2) generates his or her own key pair (ÖSM1, PSM1), (ÖSB2, PSB2), which comprises a secret part (PSM1, PSB2, private key) and a non-secret part (ÖSM1, ÖSB2, public key).

The public key (ÖSM1, ÖSB2) enables anyone to encrypt data for the owner of the private key, to check the digital signature thereof or to authenticate the owner. Related to the data exchange between the ventilator or anesthesia device and the measuring system, this means that the public key (ÖSM1) of the measuring system makes it possible for the ventilator or anesthesia device to encrypt data for the measuring system (owner of the private key PSM1), to check a digital signature (SEM1) of the measuring system and thus to unambiguously authenticate the measuring system (M1) at the ventilator or anesthesia device (B2). This means, furthermore, that the public key (PSM2) of the ventilator or anesthesia device makes it possible for the measuring system to encrypt data for the ventilator or anesthesia device (owner of the private key PSB2), to check a digital signature (SEB2) of the ventilator or anesthesia device and thus to unambiguously authenticate the ventilator or anesthesia device (B2) at the measuring system (M1).

The private key makes it possible for its owner (M1, B2) to decrypt data encrypted with the public key, to generate digital signatures or to authenticate itself. Related to the data exchange between the ventilator or anesthesia device and the measuring system, this means that the private key of the ventilator or anesthesia device (PSB2) makes it possible for the ventilator or anesthesia device to decrypt data, which the measuring system has encrypted with the public key of the ventilator or anesthesia device (ÖSB2), as well as to generate the digital signature (SEB2) unambiguously belonging to the ventilator or anesthesia device and to authenticate itself by means of this digital signature (SEB2) at the measuring system as a ventilator or anesthesia device of a certain group of ventilators or anesthesia devices or as a certain ventilator or anesthesia device. It means, furthermore, that the private key of the measuring system (PSM1) makes it possible for the measuring system to decrypt data, which the ventilator or anesthesia device has encrypted with the public key of the measuring system (ÖSM1), as well as to generate the digital signature (SEM1) unambiguously belonging to the measuring system and to unambiguously authenticate itself by means of the digital signature (SEM1)

at the ventilator or anesthesia device as a measuring system of a certain group of measuring systems or as a certain measuring system.

According to the present invention, a medical system has
a measuring system with an interface to a sensor module, with a first (measuring system) memory, with a first (measuring system) data processing unit, with a first (measuring system) data-providing (data output) unit and preferably with a second (measuring system) data-receiving unit,
a transmission channel, and
a ventilator or anesthesia device with a first (ventilator/anesthesia device) data-receiving unit, with a second (ventilator/anesthesia device) data processing unit, with a second (ventilator/anesthesia device) memory, with a control unit and preferably with a second (ventilator/anesthesia device) data-providing (data output) unit.

The medical system is configured for providing and exchanging data in a data network between the measuring system and the ventilator or anesthesia device.

According to the present invention, the medical system provides an authentication of the measuring system at the ventilator or anesthesia device and an influencing of a control of the performance of the ventilation by the ventilator or anesthesia device on the basis of a sensor signal, which is provided by the sensor module and which preferably indicates an oxygen saturation in the blood of a living being or a carbon dioxide concentration in the gas exhaled by a living being.

The measuring system has the interface to the sensor module, the first memory, the first data processing unit and the first data output unit.

The interface is configured to detect at least one sensor signal provided by the sensor module. A physiological parameter of a living being, preferably an oxygen saturation in the blood of a living being, or a carbon dioxide concentration in the gas exhaled by a living being can be indicated by the at least one sensor signal.

The at least one sensor signal may represent in this case the physiological parameter directly as a direct measured variable as well as indicate the physiological parameter indirectly as a sensor signal processed by means of a signal processing (amplification, filtering, level conversion).

The first data processing unit is configured to generate at least one first data set on the basis of the at least one sensor signal. The first data processing unit is configured to sign a first (measuring system) data item derived from the at least one first data set with a private key (PSM1) of a first (measuring system) asymmetric encryption pair, which private key is assigned to the measuring system and is provided by the first memory. The first data output unit is further configured to provide the signed first data item for the transmission channel.

The ventilator or anesthesia device has the first data-receiving unit, the second data processing unit, the second memory and the control unit.

The first data-receiving unit is configured to receive the signed first data item from the transmission channel. The first data-receiving unit or the second data processing unit is configured to extract a first (measuring system) signature element from the received first data item. The second data processing unit is further configured to check by means of a public key (ÖSM1) of the first asymmetric encryption pair, which public key is provided by the second memory and is associated with the measuring system, further on the basis of the at least one first data set extracted from the first data item and of the first signature element, to check whether the first signature element corresponds to the public key (ÖSM1), and to check on the basis of the first signature element and of additional classification data provided by the second memory whether the sensor module belongs to a certain sensor module or to a certain class of measuring systems. The control unit is configured to control or influence at least one setting value and/or operating parameter of the ventilator or anesthesia device, which setting value and/or operating parameter can be used to carry out a ventilation, on the basis of the at least one sensor signal contained in the at least one first data set as a function of a first checking result.

Table 1a below illustrates as an example the manner in which the control unit takes into account the classification data and the resulting belonging of the measuring system to a certain class of measuring systems of three different types of measuring systems for controlling or influencing a ventilation in a closed control loop ($SpO_2$ closed loop ventilation). The control unit brings about the provision of a necessary inspiratory oxygen percentage ($FiO_2$) adapted for the particular patient by means of a setting of an oxygen concentration in the breathing gas. A fraction of inspired oxygen of $FiO_2=0.2$ corresponds in this case to an oxygen concentration of 21% (room air). Based on the classification data, three exemplary types of $SpO_2$ measuring systems are distinguished. The respective type-dependent control bandwidth is seen in Table 1a for setting $FiO_2$ at the ventilator as a tolerance range around a setting range of an oxygen concentration of 39% ($FiO_2$) dispensed during the inhalation.

Type 1 is a measuring system of high reliability and measuring accuracy, in which data and diagrams are provided at a data rate in the range of 0.5-100 output values per second. In addition, type 1 has a very good suppression of external influencing variables, for example, heartbeat, finger/hand motions, and great robustness against electromagnetic radiation (EMC).

When a measuring system of type 1 is used, an oxygen saturation ($SpO_2$) target value of 95% can be reached in the closed control loop ($SpO_2$ closed loop ventilation) with a deviation of ±2%.

Type 2 is a measuring system of medium measuring accuracy. Type 2 has good heartbeat suppression.

Type 3 is a simple measuring system, with which only a subsidiary (daughter) display of previously detected $SpO_2$ measured values transmitted to the ventilator is made possible at the ventilator.

These differences in the three exemplary types of measuring systems are stored in the classification data in the memory of the ventilator or anesthesia device, as is shown as an example in Tables 1a, 1b, 1c and 2 below.

TABLE 1a

| Setting value | Measuring system | | |
| --- | --- | --- | --- |
| | Type 1 | Type 2 | Type 3 |
| $FiO_2$ setting range | 21%-100% | 39% ± 8% | 39% ± 0% |

It is seen in Table 1a that a restriction or limitation in the $FiO_2$ setting range is not necessary with the measuring system of type 1 in the closed control loop ($SpO_2$ closed loop ventilation), because values of the oxygen saturation ($SpO_2$) detected by the oxygen saturation ($SpO_2$) detected with the measuring system of type 1 are made available to the ventilator or anesthesia device as reliable values at a sufficient data rate, so that the dimensioning of the control loop in the ventilator, for example, with the dimensioning of KP and TN, is adapted to this data rate, and the control of the quantity of oxygen can thus take place sufficiently dynamically corresponding to the physiological requirements. It is thus ensured in the medical system comprising an $SpO_2$ measuring system and a ventilator or anesthesia device that both the measured value acquisition and changes based on this measured value acquisition in the oxygen percentages ($FiO_2$) effected by means of $O_2$ dispensing in the closed control loop take place with a short delay and with a sufficient setting accuracy in respect to the physiology of oxygenation in the blood gas exchange of the patient.

It follows from this that supplying the patient with a sufficient quantity of breathing gas and oxygen is ensured at any time.

Table 1a shows, moreover, that when a measuring system of type 2 is used, it is necessary to limit the $FiO_2$ setting range in the closed control loop ($SpO_2$ closed loop ventilation).

As a result, it is also possible to use the measuring system of type 2 with medium accuracy, whose measuring accuracy does not make possible, for example, a continuous control to a target value of an oxygen saturation ($SpO_2$), as in the case of a measuring system of type 1 with a narrow control range, i.e., for example, ±2%, because the drawbacks of measuring system 2 compared to measuring system 1, which drawbacks are effective for the control, can be compensated, so to speak, by the limitation in the $FiO_2$ setting range. A "freak value," which may arise as an $FiO_2$ setting value in the course of the control on the basis of a measurement error, which may occur, for example, on the basis of insufficient robustness of the measuring system 2 against electromagnetic radiation, is "cushioned," so to speak, by the $FiO_2$ setting value limitation in the control of ventilation in a closed control loop ($SpO_2$ closed loop ventilation), i.e., it is ineffective in respect to the supply of the patient with a sufficient quantity of breathing gas and oxygen. When a measuring system of type 3 is used, an open $SpO_2$ control loop ($SpO_2$ open-loop ventilation) is obtained, and no $FiO_2$ setting range is provided. The $FiO_2$ setting value of the controller is set at the target value of, e.g., 39%. The oxygen saturation $SpO_2$ is displayed for display purposes only at the ventilator or anesthesia device, and monitoring with corresponding alarm generation at the ventilator or anesthesia device may be made possible.

In a preferred embodiment, the control unit is configured, as a function of the first checking result, to adapt an alarm organization and/or adaptations during the performance of the alarm organization during the operation of the ventilator or anesthesia device.

Table 1b below shows as an example how the control unit takes the classification data of the three different types of measuring systems into account for an alarm organization during a ventilation in a closed control loop ($SpO_2$ closed loop ventilation).

TABLE 1b

| Setting value | Measuring system | | |
| --- | --- | --- | --- |
| | Type 1 | Type 2 | Type 3 |
| Priority $Vt_{Low}$ alarm | low | mid | high |
| Priority $MV_{Low}$ alarm | low | high | high |

An $MV_{Low}$ alarm indicates the case in which the ventilator or anesthesia device determines that the minute volume (MV) of breathing gas administered to the patient, i.e., the product of respiration rate (RR) and the tidal volume (Vt), is too low compared to a preset value. A $Vt_{Low}$ alarm is often used in addition to a ventilation mode with volume guarantee (VG). A comparison is made in this case between the supplied volume and the Vt setting value over a predefined time period, and an alarm is then generated when the supplied volume is below a predefined threshold value, preferably 90% of the Vt setting value during the predefined time period.

In case of ventilation in a closed control loop ($SpO_2$ closed loop ventilation), an oxygen saturation of $SpO_2>95\%$ in the blood over a rather long time period, which oxygen saturation was determined in a reliable information situation concerning signal detection, signal processing, measuring accuracy, data rate and data transmission, i.e., for example, with a measuring system of type 1, indicates that the blood gas exchange of the patient is undisturbed. Both a state of health or recovery process of the patient and the fact that the interaction of $SpO_2$ detection with the measuring system of type 1 and of the ventilation by the ventilator or anesthesia device by means of control and dispensing is essentially error-free in the medical system can be inferred from this. It follows from that, that the signaling at the ventilator or anesthesia device of an $MV_{Low}$ alarm and/or of a $Vt_{Low}$ alarm can be signaled with lower priority in case of use with a measuring system of type 1 than in case of applications with a measuring system of type 2 or of type 3. Such a prioritization is made in Table 1b as an example as a three-level classification to the levels "Low," "Mid" and "High." "Low" may be implemented, for example, such that no signaling of the $MV_{Low}$ alarm and/or of the $Vt_{Low}$ alarm takes place at the ventilator or anesthesia device. Signaling of the $MV_{Low}$ alarm and/or of the $Vt_{Low}$ alarm takes place in any case at the ventilator or anesthesia device at the "High" level, and, for example, the acoustic signaling of the $MV_{Low}$ alarm and/or of the $Vt_{Low}$ alarm may be carried out at the ventilator or anesthesia device at the "Mid" level as a so-called "silent alarm" (muting) or as an alarm with a time delay (alert delay).

According to another preferred embodiment, the control unit is configured, as a function of the first checking result, for an adaptation of physiological alarm threshold values, which are preferably representative of an oxygen saturation in the blood of a living being or of a carbon dioxide concentration in the exhaled gas, during the control of the ventilation during an operation of the ventilator or anesthesia device on the basis of the at least one sensor signal. Such an adaptation of alarm threshold values is, for example, an adaptation of an alarm threshold value of the oxygen saturation $SpO_2$ on the basis of the type of the measuring system. Table 1c below shows as an example, with inclusion of types of measuring systems, how the control unit can take into account alarm threshold values belonging to the oxygen saturation $SpO_2$ as well as ranges of variation and permissible tolerances of these values, which are due to the measuring accuracy of the particular measuring system, on the basis of the type of the measuring system. The measuring system of type 2 can be classified in this case concerning the $SpO_2$ alarm threshold value and the permissible tolerance thereof between the measuring systems of type 1 and type 3.

TABLE 1c

| Setting value | Measuring system | | |
| --- | --- | --- | --- |
| | Type 1 | Type 2 | Type 3 |
| $SpO_2$ alarm threshold value and tolerance | 92% ± 1% | —/— | 95% ± 3% |

According to a preferred embodiment, the interface or the first data processing unit are configured to determine a quality level (Signal Quality level, SQ level) on the basis of the sensor signal and to provide the quality level (SQ level) in the at least one first data set.

The quality level (signal Quality level, SQ level) is an indicator, which indicates the signal quality of the signal transmitted by the measuring system. The signal quality may be comprised, for example, by a high percentage of noise superimposed to the useful signal, so that an unfavorable signal-to-noise ratio (SNR) is obtained, which can correspondingly be indicated by means of the quality level (low signal quality). An unfavorable positioning at a body part with low perfusion may likewise lead to an impairment of the signal quality, especially to a measured signal at the $SpO_2$ finger clip sensor with such a low signal amplitude (low signal quality) that no $SpO_2$ measured value can be determined in the sensor module. Such a situation may likewise be indicated correspondingly by means of the quality level (low signal quality). Disconnecting the $SpO_2$ finger clip sensor from the finger can be detected by the measuring system or sensor module and can correspondingly be indicated by the quality level (SQ level=(Low, No Signal)). The control unit is configured as a function of the first checking result and/or on the basis of the quality level (SQ level) provided in the at least one first data set to control or influence at least one setting value and/or operating parameter of the ventilator or anesthesia device, which setting value and/or operating parameter can be used to carry out the ventilation.

Table 2 below shows, as an example for a measuring system of type 1, how the control unit can take the quality level (SQ level) into account when the ventilation is carried out. The quality level indicates a state of a signal quality; as an example, a three-level classification to the levels "Low," "Mid" and "High" is made in this Table 2. The $FiO_2$ setting range for a measuring system of type 1 is limited in case of decreasing signal quality (SQ), so that a low signal quality (SQ=low) leads to an $FiO_2$ setting range just as in case of a measuring system of type 3.

TABLE 2

| Setting value | Measuring system of type 1, SQ level | | |
| --- | --- | --- | --- |
| | high | mid | low |
| $FiO_2$ setting range | 21%-100% | 39% ± 8% | 39% ± 0% |

According to another preferred embodiment, the medical system provides an authentication of the ventilator or anesthesia device at the measuring system for adapting a signal detection, a signal processing or for adapting alarm threshold values when an alarm organization is carried out and/or the alarm organization of the sensor module is carried out. A second data output unit is provided for this in or at the ventilator or anesthesia device and a second (measuring system) data-receiving unit is provided at the measuring system. The second data processing unit is configured to generate at least one second data set on the basis of at least one information signal provided by the ventilator or anesthesia device. A type of the ventilator or anesthesia device and/or a state or a current mode of operation of the ventilator or anesthesia device can be indicated by the at least one information signal. The second data processing unit is configured to sign a second data item derived from the at least one second data set with a private key (PSB2) of a second asymmetric encryption pair, which private key is assigned to the ventilator or anesthesia device and is provided by the second memory. The second data output unit is configured to provide the signed second data item to the transmission channel. The second data-receiving unit is configured to receive the at least one signed second data item of the ventilator or anesthesia device. The second data-receiving unit or the first data processing unit is configured to extract a second signature element from the at least one second data item received. The first data processing unit is further configured to check, by means of a public key (ÖSB2) of a second asymmetric encryption pair, which public key is provided from the first memory and is assigned to the ventilator or anesthesia device, and, further on the basis of the at least one second data set extracted from the second data item and of the second signature element, whether the second signature element corresponds to the public key (ÖSB2). The first data processing unit is configured to perform a checking, on the basis of the second signature element and by identification data provided by the first memory, to determine whether the ventilator or anesthesia device is identical to a certain ventilator or anesthesia device. The first data processing unit or the interface is configured to provide a second checking result of the checking. The first data processing unit or the interface is configured, as a function of the second checking result, to adapt a signal detection and/or a signal processing of the sensor signal during the generation of the at least one first data set and/or to adapt alarm threshold values when an alarm organization is carried out and/or when the alarm organization is carried out during the operation of the sensor module.

The authentication of the ventilator or anesthesia device at the measuring system and the use of the information signal in interaction with the identification data offers the advantage that, adapted to requirements imposed on the signal detection of the oxygen saturation by the measuring system, which the ventilator or anesthesia device has concerning the control in the closed loop ($SpO_2$ closed loop ventilation), the signal detection and the signal processing with signal amplification and signal filtering in the measuring system can be configured with respect to an optimal interaction of the ventilator or anesthesia device and the measuring system in the medical system. For example, the signal filtering can thus be adapted in the signal processing of the measuring system with respect to the preferably digital filter types (IIR, FIR, high-pass, low-pass, band-pass) used subsequently for the signal detection and with respect to the limit frequencies thereof and concerning the durations used for the averaging (moving average, repeating average) to different requirements needed by certain different types of ventilators or anesthesia devices for using the transmitted $SpO_2$ signal in the closed control loop ($SpO_2$) closed loop ventilation.

The authentication of the ventilator or anesthesia device at the measuring system offers the further advantage that the alarm organization of the measuring system and the ventilator or anesthesia device can be coordinated with one another. An alarm, which is based, for example, on a malfunction in the measuring system, for example, a disconnection of an SpO$_2$ finger clip sensor from the finger at the measuring system, which is detected by the measuring system, can be signaled in this manner within the medical system by a so-called "silent alarm," i.e., with a deactivation of the acoustic signal generation at the measuring system, because the alarm is additionally also outputted at the ventilator or anesthesia device, preferably as an acoustic ("loud") alarm.

While a certain type of a ventilator or anesthesia device affects, so to speak, a basic configuration of the data acquisition and data processing for the interaction of the ventilator or anesthesia device and the measuring system in the medical system, a state or a current mode of operation of the ventilator or anesthesia device can affect the manner of functioning of the measuring system during the ongoing operation of the interaction of the ventilator or anesthesia device and the measuring system in the medical system. For example, an adaptation of the alarm generation may take place on the measuring system in situations in which an alarm is performed (generated and issued) on the ventilator or anesthesia device with disconnection of the patient with ventilation tubes, for example, due to actions taken by the nursing staff (secretion suction, change of dressing, repositioning, blood pressure measurement on the upper arm) or by the clinical staff. For example, a blood pressure measurement on the upper portion of the arm may somehow act on the finger of which the SpO$_2$ sensor is attached by means of a finger clip so as to affect the measurement with this SpO$_2$ sensor and possibly lead to a false alarm. An adaptation of the alarm generation on the measuring system, for example, in the form of carrying out the above-described adaptation as a so-called "silent alarm" (muting) or alarm with a time delay (alert delay) may be carried out in such a case.

In another preferred embodiment, the first checking result of the checking performed to determine whether the sensor module belongs to a certain measuring system or sensor module or to a certain class of measuring systems or sensor modules can be indicated by the at least one information signal. This embodiment provides the advantageous possibility that an authenticated information showing the type of measuring system from the group of measuring systems under which the ventilator or anesthesia device classified the measuring system on the basis of the preceding authentication of the measuring system by means of the first signature element is made available to the measuring system by the ventilator or anesthesia device. A possibly incorrect assignment can be detected by the measuring system via this feedback on the basis of the classification data and corrected by means of subsequent actions, for example, a repetition of the authentication. Corresponding information may additionally also be provided by the measuring system and/or the ventilator or anesthesia device for the user by means of an output of a corresponding warning.

In another preferred embodiment, the first data processing unit is configured to sign and encrypt the first data item with the public key (ÖSB2) of the second asymmetric encryption pair, which public key is assigned to the ventilator or anesthesia device.

The first data output unit is configured to provide the encrypted, signed first data item for the transmission channel. The first data-receiving unit is configured to decrypt the signed and encrypted first data item received by means of the private key (PSB2) of the second asymmetric encryption pair, which private key is provided by the first memory and to provide it as the at least one first data set for the control unit. This configuration of the data transmission with an encryption with an asymmetric encryption method offers the advantage that the data transmission within the medical system via the data network cannot be utilized in a simple manner by third parties, especially by unauthorized third parties. Eavesdropping on the data transmission in the data network is prevented by means of the asymmetric encryption. Especially in embodiments in which, for example, personal data of the patient shall be transmitted from the measuring system to the ventilator or anesthesia device by means of the data network, it may be useful and appropriate for reasons of data protection to prevent a possible abuse of personal data, for example, age, clinical picture, gender, body weight, height, length of hospitalization, by unauthorized persons.

In another preferred embodiment, the second data processing unit is configured to encrypt the second data item with the public key (ÖSM1) of the first asymmetric encryption pair, which public key is assigned to the measuring system, and the second data output unit is configured to provide the encrypted, signal second data item to the transmission channel. The second data-receiving unit or the first data processing unit is configured to decrypt the signed and encrypted second data item received from the transmission channel by means of the private key (PSM1) of the first asymmetric encryption pair, which private key is provided by the second memory, and to provide it as the at least one second data set for the first data processing unit or for the interface. It can be ensured by such an encryption of the information signal of the ventilator or anesthesia device on the way over the data network to the measuring system that, for example, the adaptation of the alarm generation (silent alarm) as well as the adaptation of the signal detection and signal processing (signal amplification, signal filtering, averaging) are not made possible by an access from the outside to the data network by means of a manipulation. These encryptions, just like the authentication and the identification, increase the functional reliability in the interaction of the ventilator or anesthesia device with the measuring system in the medical system.

As a result, both an unambiguous assignment of measuring systems and ventilator or anesthesia device and securing of the transmission of the data and data sets transmitted between these two devices interacting in the medical system are made possible by the use of asymmetric encryption pairs.

In another preferred embodiment, the transmission channel has at least one component or a plurality of components, which are configured to store or temporarily store signals, data and/or information for a data distribution and data organization as well as to organize the data exchange in the data network between the measuring system and the ventilator or anesthesia device, for the assignment and storage of data, especially data packets. Components in the data network are, for example, addressing and switching devices (switches, routers, multiplexing units) as well as temporary memories and signal amplifiers (hubs), as well as servers and hard drives as data servers, file servers and other network components.

In another preferred embodiment, data are provided and exchanged in the data network with the use of a network data transmission protocol (TCP). The data transmission with redundant transmission pathways via a plurality of network nodes (routers) is organized in this case by the transmission control protocol (TCP, Transport Layer) and the Internet Protocol (IP, network Layer).

In another preferred embodiment, the classification data are provided for the second memory by means of the transmission channel and by means of the at least one component or the plurality of components. Such a configuration is obtained, for example, such that the classification data belonging to the measuring systems are distributed by a server in the data network to a plurality of ventilators or anesthesia devices. This leads to the advantage that changes in the classification data, for example, the integration of additional measuring systems in the classification data via the data network, for example, via a central broadcasting action, can be distributed centrally in the data network without a local configuration action on the particular ventilator or anesthesia device.

In another preferred embodiment, the identification data are provided for the first memory by means of the transmission channel and by means of the at least one component or the plurality of components. Such an embodiment is obtained, for example, such that the identification data belonging to the ventilators or anesthesia devices are distributed by a server in the data network to the measuring systems. This offers the advantage that changes in the identification data, for example, the integration of additional measuring systems in the identification data via the data network, can be distributed centrally in the data network, for example, via a central broadcasting action without a local configuration action on the particular measuring system.

The embodiments described represent special embodiments of the medical system according to the present invention both each in itself and combined with one another. Advantages arising from the combination or combinations of a plurality of embodiments and further embodiments are likewise covered by the inventive idea, even if not all possible combinations of embodiments are explained in detail.

The present invention will be explained in more detail in the following figures and in the corresponding descriptions of the figures without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
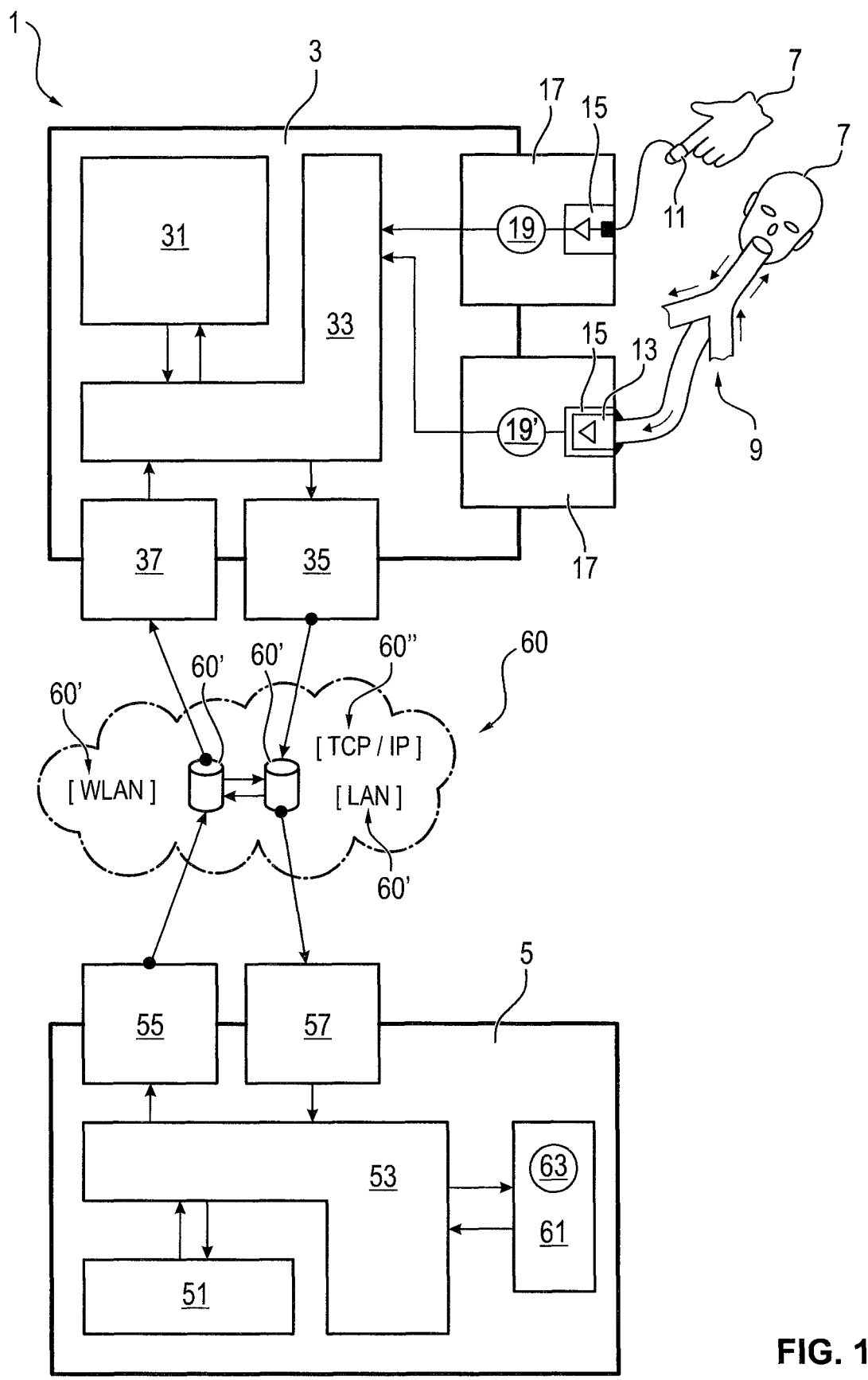
FIG. 1 is a schematic view of a medical system according to the invention.

Referring to the drawings, FIG. 1 shows a medical system 1.

The medical system 1 comprises a measuring system 3 (M1) and a ventilator or anesthesia device 5 (B2). Measured values, which can be detected by a sensor 11, which is configured for measuring an oxygen saturation ($SpO_2$) in the blood of a patient 7, reach the measuring system 3 as sensor signals 19 via an interface 17 by means of a sensor module 15. Furthermore, sensor signals 19', which are detected by an optional sensor 13 for detecting a carbon dioxide concentration ($etCO_2$) in the breathing gas of the patient 7, reach the measuring system 3 via this interface 17. In an embodiment with the optional sensor 13 ($CO_2$ sensor), the carbon dioxide concentration in the breathing gas of the patient 7 is provided at a ventilation tube system 9 close to the mouth of the patient 7 by means of a sampling tube and delivered to the sensor 13 for detecting the carbon dioxide concentration. This delivery takes place by means of a pump, not shown in this FIG. 1. A signal and data preprocessing unit, for example, a signal amplification unit, is integrated in the sensors 13, 15. From the sensor module 15 and the sensor 13, the sensor signals 19, 19' reach a first (measuring system) data processing unit 33 from the sensor module 15 and the sensor 13. The measuring system 3 is configured, for example, as a so-called pulse oximeter for detecting the oxygen saturation in the blood or as a so-called capnometer or oxi-capnometer for detecting a carbon dioxide concentration or carbon dioxide and oxygen concentration in the breathing gas. A typical embodiment is a so-called physiological patient monitor, which measures additional physiological parameters, such as heart rate, EKG, blood pressure (NIBP), in addition to the above-mentioned oxygen saturation and/or carbon dioxide and oxygen concentration. The first data processing unit 33 is connected to a first (measuring system) memory 31. The first data processing unit 33 provides as an additional interface a first (measuring system) data output unit 35 as well as a second (measuring system) data-receiving unit 37. Via these two units 35, 37, the measuring system 3 is able to exchange data with other participants (B2) in the data network 60 via a transmission channel or a data network 60. For example, components 60', which make possible the addressing, assignment and storage of data, especially data packets, are provided for this in the data network 60. A data transmission protocol 60" (TCP/IP) is usually used for transmitting and transferring data in the data network 60 and components 60' thereof. Components 60' in the data network are, for example, addressing and switching devices (switches, routers, multiplexing units) as well as temporary storage devices and signal amplifiers (hubs), servers and hard drives as data servers, file servers and other network components. The ventilator or anesthesia device 5 has as components a second (ventilator/anesthesia device) memory 51, a second (ventilator/anesthesia device) data processing unit 53 and a control unit 61. A second (ventilator/anesthesia device) data output unit 55 and a first (ventilator/anesthesia device) data-receiving unit 57 are provided for the data exchange with the data network 60. The first data output unit 35 makes available the sensor signals 19, 19', which indicate physiological data of the patient 7, namely, the oxygen saturation ($SpO_2$) in the blood of the patient 7 or also the optional carbon dioxide concentration ($etCO_2$) in the gas exhaled by the patient 7, to the data network or transmission channel 60. The first data-receiving unit 57 receives sensor signals 19, 19' embedded in a data set 39 generated by the first data output unit 35 (FIG. 2a) as well as "data items" 39', 39'' (FIG. 2a), 39''' (FIG. 2b) generated from the data set 39 (FIG. 2a) from the data network 60 and makes these available for the control unit 61 for generating setting values 43 (FIG. 2a, FIG. 2b) at the ventilator or anesthesia device 5.

Figure 2A:
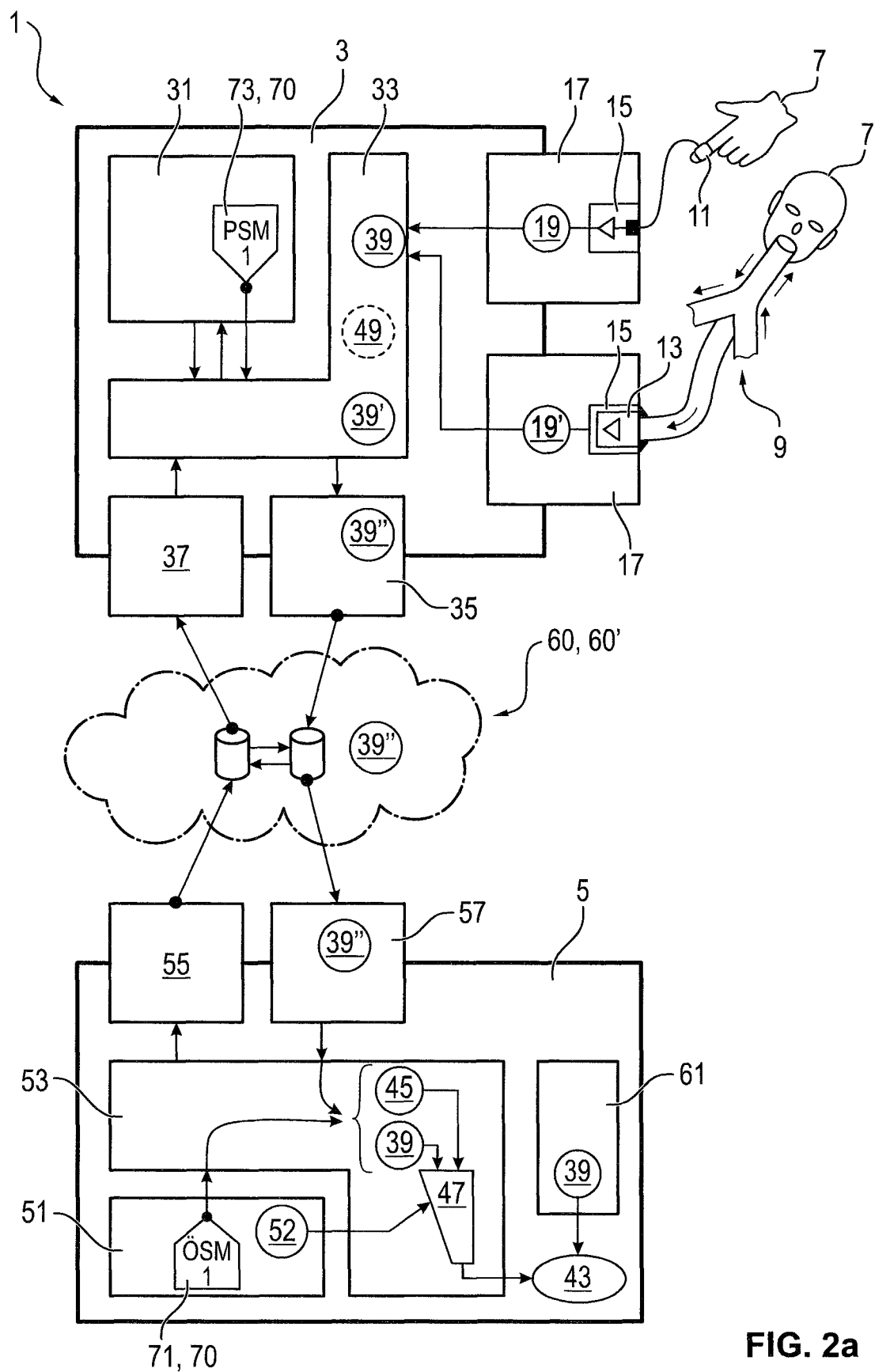
FIG. 2a is a schematic view showing a first variant of data transmission from the measuring system to the ventilator or anesthesia device.

The control unit 61 is configured in the ventilator or anesthesia device 5 to perform and carry out the ventilation of a patient 7 via a ventilation tube system 9. When such a mechanical or mandatory ventilation of the patient 7 is carried out, air to be inhaled is fed by means of the ventilation tube system 9 from the ventilator or anesthesia device 5 to this patient 7 and air exhaled by the patient 7 is removed from this patient 7 and sent to the ventilator or anesthesia device 5. This pneumatic connection of the ventilator or anesthesia device 5 by means of the ventilation tube system 9 is indicated only schematically in this FIG. 1 for clarity's sake. An inhalation ventilation tube delivers the air to be inhaled to the patient 7, and an exhalation ventilation tube delivers the exhaled air from the patient 7 back to the ventilator or anesthesia device 5. Valves and additional actuators as well as sensors, likewise not shown in FIG. 1, are present in the ventilator or anesthesia device 5 for controlling the ventilation. These include, for example, an inspiratory flow sensor and/or an expiratory flow sensor as well as an inspiratory and/or expiratory pressure sensor in order to control or regulate pressure conditions and flow conditions in the ventilation tube system 9 to the patient 7. In addition, dispensing devices (reciprocating pumps, blower drives, servo valves) are present for dispensing breath and for adding oxygen and ambient air or compressed air in order to control or regulate the oxygen concentration in the gas to be inhaled by the patient 7. The oxygen concentration in the gas inhaled by the patient is set in this case according to this embodiment shown in FIG. 1 on the basis of two measured variables, which are available as sensor signals 19, 19' from the measuring system 3. Provisions are consequently made for performing a dispensing of the oxygen concentration ($FiO_2$) to the patient 7 with the medical system shown in this FIG. 1 on the basis of the sensors 11 for measuring an oxygen saturation in the blood ($SpO_2$) of the patient 7 and/or of the optional sensor 13 for detecting a so-called end-tidal carbon dioxide concentration ($etCO_2$) in the breathing gas of the patient 7. Regulation of oxygen concentration and of additional parameters of the ventilation, such as the respiration rate (RR), minute volume (MV), ventilation pressures (Pinsp, PEEP), volumes (Vt, AMV) and ventilation times (I:E ratio) is made possible in this manner with the medical system 1. The second data output unit 55 is provided to make available, for example, status data or situation data (alarm messages, error messages, operating instructions) as information signals 63 available to the measuring system 3 via the data network 60. This may also include states concerning operating states (alarm generation situations, fault indications) or operation settings (ventilation settings, modes of ventilation, alarm threshold values) as well as information on the patient type being treated (body weight, gender, height, age), which is entered as data on the ventilator or anesthesia device 5 by the clinical staff and kept available in the ventilator or anesthesia device. It is thus shown in this FIG. 1 that a data exchange is possible in the medical system 1 from the measuring system 3 via the first data output unit 35 to the first data-receiving unit 57. Furthermore, FIG. 1 shows that a data exchange is possible from the ventilator or anesthesia device 5 to the measuring system 3 via the second data output unit 55 and the second data-receiving unit 37. The second data-receiving unit 37 receives for this the information signals 63 of the ventilator or anesthesia device 5 embedded in a data set 59 (FIG. 3a) generated by the second data output unit 55, as well as "data items" 59', 59" (FIG. 3a), 59''' (FIG. 3b) generated from the data set 59 (FIG. 2a) from the data network 60 and it makes these available for the first data processing unit 33 in the measuring system 3. While FIG. 1 shows the medical system 1 with the measuring system 3 and with the ventilator or anesthesia device 5 in a schematic functional interaction in a data network 60, it is shown in the further FIGS. 2a, 2b, 3a, 3b how the data transmission takes place via the data network 60 by means of identification and authentication in such a way that the ventilator or anesthesia device 5 can check the information of the measuring system 3 to determine whether and by which measuring system 3 the data were sent. In the same way, it is shown that the measuring system 3 can check whether and by which ventilator or anesthesia device 5 information had been transmitted via the data network 60 as data to the measuring system 3. FIGS. 2a and 3a use so-called asymmetric encryption pairs 70, 80 to identify the sending device 3, 5. These asymmetric encryption pairs 70, 80 are additionally used in FIGS. 2b and 3b to encrypt the data transmission in the data network 60 in addition to the identification/authentication.

FIG. 2a shows the transmission pathway of a transmission of sensor signals 19, 19' as a first (measuring system) data set 39 or data item 39' from the measuring system 3 in the medical system 1 via the data network 60 and components 60' thereof as a first (measuring system) signed data item 39", which contains identification information concerning the measuring system 3, to the ventilator or anesthesia device 5.

Figure 2B:
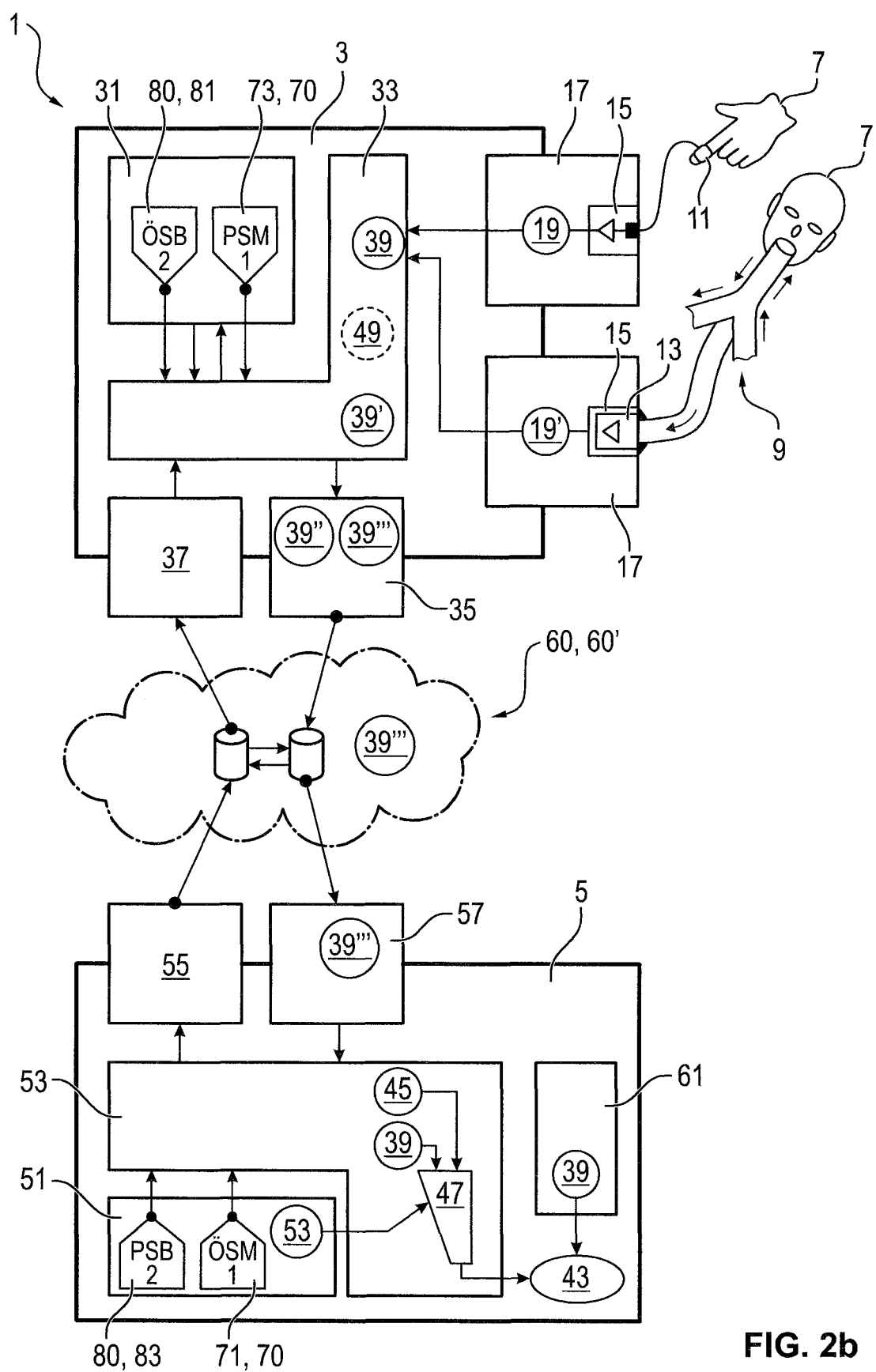
FIG. 2b is a schematic view showing a second variant of a data transmission from the measuring system to the ventilator or anesthesia device.
Figure 3A:
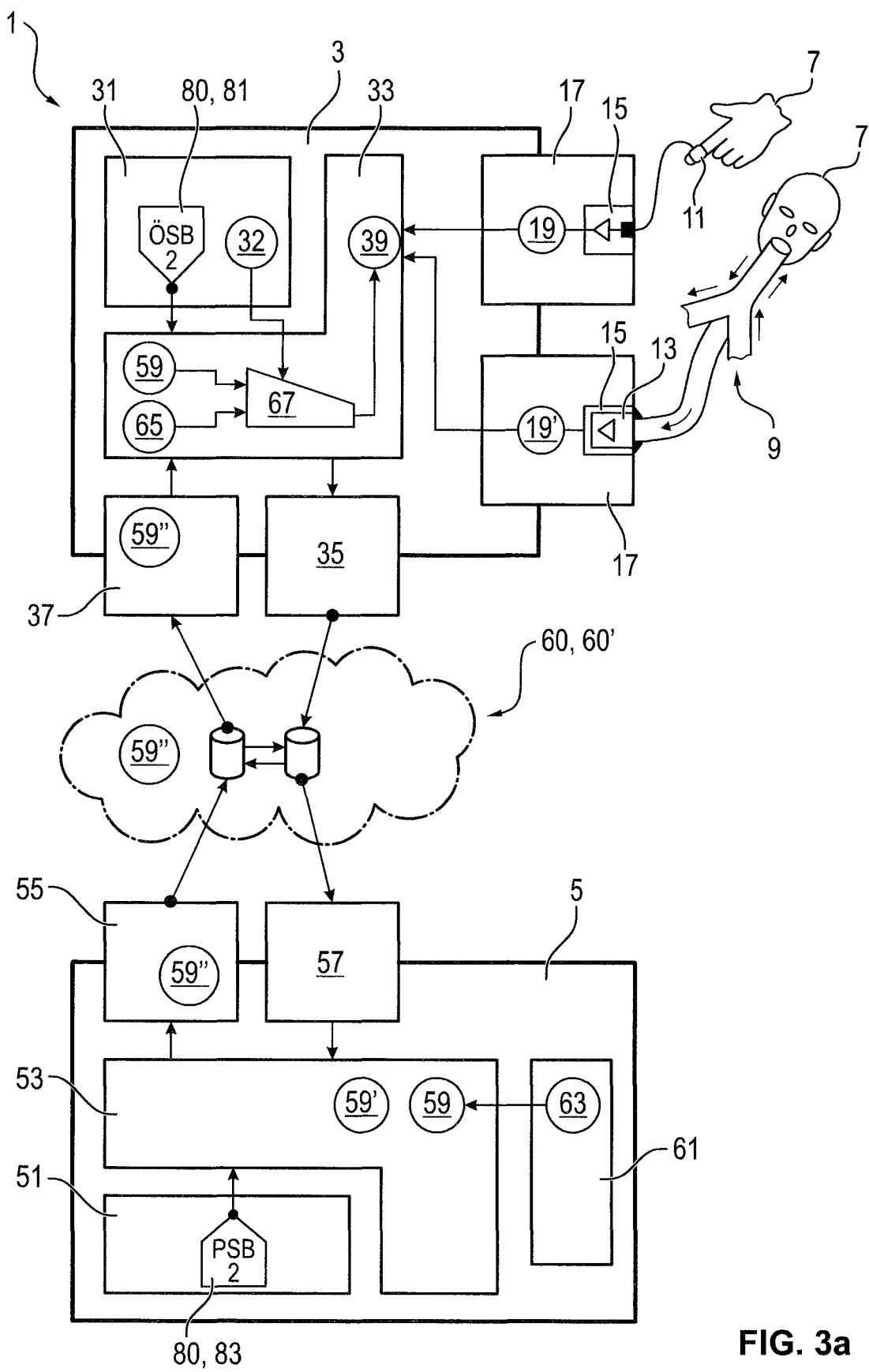
FIG. 3a is a schematic view showing a first variant of a data transmission from the ventilator or anesthesia device to the measuring system.

FIG. 2b shows that the first data item 39 is transmitted from the measuring system 3 according to FIG. 2a as a first (measuring system) encrypted data item 39''' to the ventilator or anesthesia device 5 in addition to the identification information via the data network 60.

FIG. 3a shows the data transmission from the ventilator or anesthesia device 5 to the measuring system 3, wherein an information signal 63 with identification information is transmitted as a second signed data item 59", which contains identification information concerning the ventilator or anesthesia device 5, to the measuring system 3 via the data network 60 in the medical system 1.

Figure 3B:
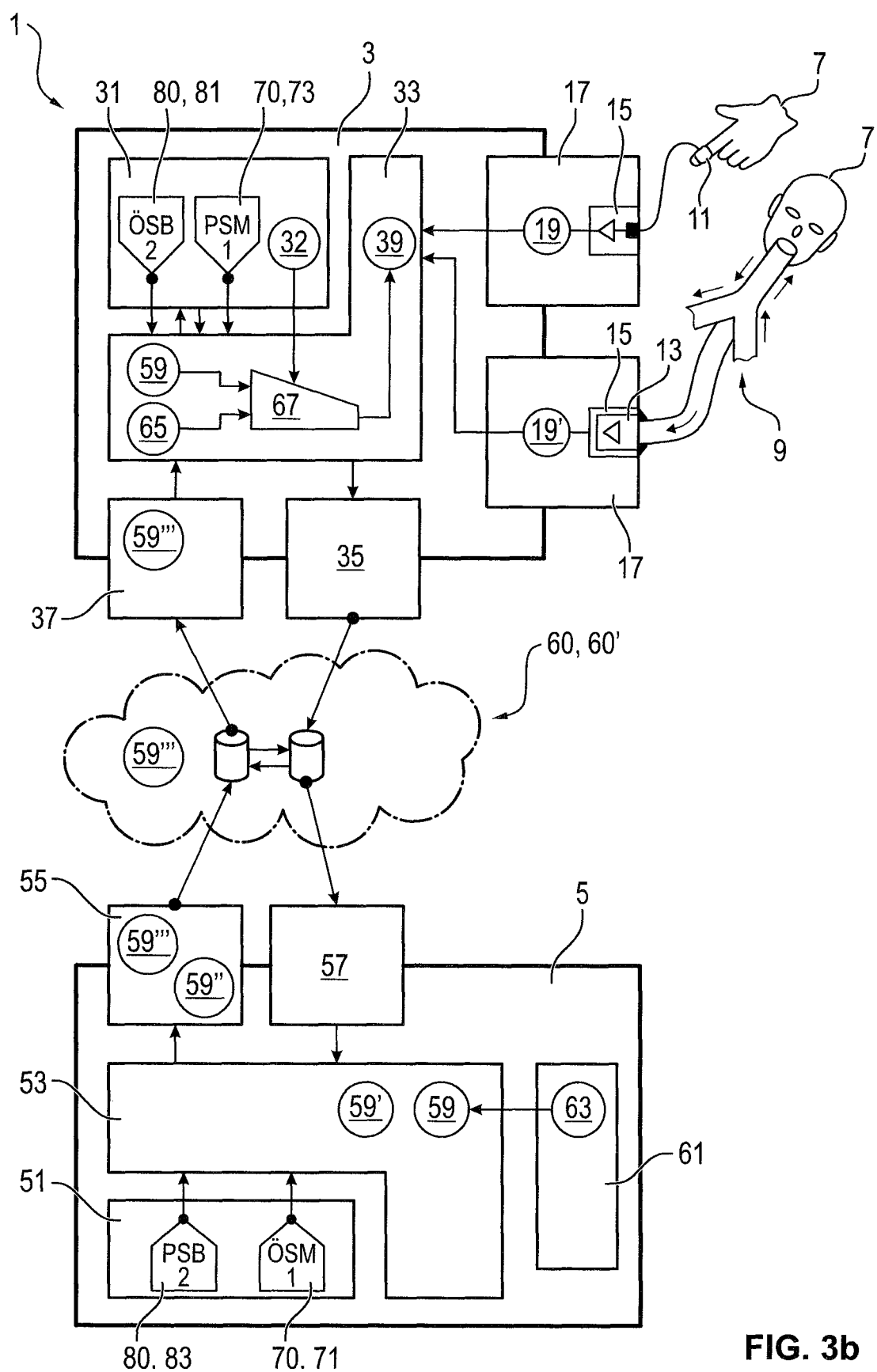
FIG. 3b is a schematic view showing a second variant of data transmission from the ventilator or anesthesia device to the measuring system.

FIG. 3b shows that the data transmission of the information signal 63 from the ventilator or anesthesia device 5 according to FIG. 3a, additionally encrypted as a second encrypted data item 59''', is carried out via the data network 60 from the ventilator or anesthesia device 5 to the measuring system 3.

FIGS. 2a, 2b, 3a, 3c will now be described. Identification or authentication of the measuring system 3 against the ventilator or anesthesia device 5 or of the ventilator or anesthesia device 5 against the measuring system 3 as well the description of the encryption of the data transmission in the data network 60 are provided.

The same basic components that were shown above in FIG. 1 and described in connection with this FIG. 1 are shown in FIGS. 2a, 2b, 3a, 3b. Identical components in FIGS. 1, 2a, 2b, 3a, 3b are designated by the same reference numbers in FIGS. 1, 2a, 2b, 3a, 3b.

FIG. 2a shows how sensor signals 19, 19' are transmitted with the measuring system 3 to the ventilator or anesthesia device 5 via the data network 60 in the arrangement of a medical system 1 with a measuring system 3 and with a ventilator or anesthesia device 5, which arrangement is shown in FIG. 1.

The sensor signals 19 ($SpO_2$) and 19' ($etCO_2$) are converted by a first (measuring system) data processing unit 33 into a data item 39. This conversion takes place such that digital data are generated from the sensor signals 19, 19' and a first (measuring system) data set 39 can thereby be formed. The first data set 39 is processed further in the first data processing unit 33 such that a private code (PSM1) 73 of a first (measuring system) asymmetric encryption pair (ÖSM, PSM1) 70, which is stored in the first memory 31 of the measuring system 3, is combined or fitted together with the first data set 39 such that a first (measuring system) data item 39' is formed. From the first data processing unit 33, the first data item 39' reaches the first data output unit 35 for further data processing, where a first (measuring system) signed data item 39" is generated from the first data item 39' and is made available to the transmission channel or data network 60. The signed first data item 39" is received or taken over from the first data-receiving unit 57 of the ventilator or anesthesia device 5 and it is thus available as a first (measuring system) signed data item 39" in the first data-receiving unit 57. The first signed data item 39" is processed in the second data processing unit 53 by means of a public code (ÖSM1) 71 of the first asymmetric encryption pair 70, which public code is provided by the second memory 51, such that both the first data set 39 and a first (measuring system) signature element 45 (SEM1) (certificate) are extracted from the signed first data item 39". Furthermore, it is determined in the second data processing unit 53 by means of classification data 52 provided in the first memory 51 by a checking 47 whether the measuring system 3 belongs on the basis of the signature element 45 (SEM1) to a certain measuring system 3 or to a certain class, group or other defined types of measuring system 3. With the result of this checking 47 of the measuring system 3, which has transmitted the sensor signals 19, 19' in the form of the first data set 39 or first data item 39' or first signed data item 39" to the ventilator or anesthesia device 5, a setting value or an operating parameter 43 is set in the ventilator or anesthesia device 5 by the control unit 61. This takes into consideration as to the setting the setting value 43 or the operating parameter 43, whether the measuring system 3 is a certain measuring system 3 or whether the measuring system 3 belongs to a certain group or types of measuring systems. By means of the first signature element 45 and the classification data 52 belonging to this signature element 45 in the ventilator or anesthesia device 5, the control unit 61 thus creates the possibility of forming setting values 43, i.e., for example, settings of ventilation settings, such as respiration rate, pressure settings, volume settings, settings of limit values for pressure and flow rates, settings of inhalation and exhalation times on the basis of the fact that the measuring system 3 belongs to a group of measuring systems or on the basis of an unambiguous assignment to a certain, special measuring system 3. The control unit 61 can ensure that the values and data transmitted from the measuring system 3 by means of the data network also indicate sensor signals 19, 19' of the same patient 7, who is also connected to the ventilator or anesthesia device 5. The values of oxygen saturation in the blood ($SpO_2$) and carbon dioxide concentration in the breathing gas ($etCO_2$), which are detected by the measuring system 3, are advantageously displayed at the ventilator or anesthesia device 5 as physiological data of the patient 7 or are provided for output. The securing of the transmission in the transmission channel, data network 60 makes it further possible for the control unit 61 to check whether the measuring system 3 used has a reliable configuration to provide sensor signals 19, 19' in order to perform the settings of the ventilation on the ventilator or anesthesia device based on this. Concretely, this means, for example, that the oxygen saturation ($SpO_2$), which was detected as a measured signal 19 in the measuring system 3, is used as a valid value by means of the transmission with securing via the first asymmetric encryption pair (ÖSM1, PSM1) 70 in the data network 60 by the control unit 61 to carry out, for example, a regulation of the oxygen concentration at the ventilator or anesthesia device 5 on the basis of the oxygen saturation information of the sensor signal 19 only if the classification data 52 do indeed allow such a setting for this measuring system 3. This leads to a variability in the allowable setting values 43 as a function of the property data of different measuring systems 3, which property data are stored in the classification data 52 in the second memory 51. An adaptation of the setting values 43 or an adaptation of operating parameters 43 may now take place such that depending on the classification data 52, a setting range of the inspiratory oxygen concentration ($FiO_2$) is input at the ventilator or anesthesia device 5 as a function of the measuring system 3 used. If the measuring system 3 is, for example, a measuring system for oxygen saturation measurement, which measuring system makes possible a very high-quality detection of the oxygen saturation, which detection is characterized by high resolution over time (high rate of measurement, high measuring frequency), the oxygen concentration of the breathing gas ($FiO_2$) can be set or controlled or regulated by the control unit 61 in a very narrow coupling with the measured value, i.e., the sensor signals 19. If, by contrast, the measuring system 3 has another, lower measuring accuracy and/or lower rate of measurement with longer time intervals between the individual measured values of the oxygen concentration ($SpO_2$), the configuration of the regulation is to be adapted by the control unit 61, for example, such that the range of control, in which the permanent deviation of the oxygen saturation ($SpO_2$) or of the oxygen concentration in the breathing gas ($FiO_2$) shall be able to be set, is different from the setting range with the measuring system 3 of a high rate of measurement. Different means in this connection that, for example, the range around a set point of about 95%±x % of an oxygen saturation ($SpO_2$) can be configured in one measuring system with higher measuring accuracy and rate of measurement with a different control tolerance than in a measuring system in which the measured values can be detected at a lower rate of measurement or with lower measuring accuracy. This is due to the respective corresponding property data in the classification data 52 being available for the control unit 61 for different measuring systems 3.

Based on the property data in the classification data 52, certain measuring systems, especially certain $SpO_2$ measuring systems 3 with a raised quality level of data acquisition, data processing and error correction, which show a suitability for a leading measurement in a closed $SpO_2$ ventilation control loop, for example, to an $SpO_2$ target value of 95%±2%, can be distinguished by the control unit 61 of the ventilator or anesthesia device 5 from other measuring systems ($etCO_2$, $SpO_2$), especially from other $SpO_2$ measuring systems 3, on the basis of the first signature element 45 extracted from the first asymmetric encryption pair (ÖSM, PSM) 70.

Such other $SpO_2$ measuring systems 3 can only be used, for example, for an $SpO_2$ value representation and a limit value monitoring, for example, of an $SpO_2$ limit value <90%, in the data network of the data network 60. Different $FiO_2$ set value tolerances are obtained for different properties of measuring systems and different types, as is described in Table 1a.

Moreover, a quality level (SQ) 49 is shown in this FIG. 2a in the first data processing unit 33. This quality level 49 is an optional indicator, which is determined on the basis of the signals 19, 19' by the first data processing unit 33. In an optional embodiment, this quality level 49 is also included in the first data set 39 and hence also in the first data item 39' as well as in the first signed data item 39", so that this quality level 49 is also available to the second data processing unit 53 in the ventilator or anesthesia device 5 after transmission via the data network 60 to also configure the setting values 43 or operating parameters 43 of the ventilator or anesthesia device as a function of this quality level 49.

Configuring the setting values 43 as a function of the quality level (SQ) 49 may be carried out, for example, such that, similarly to what was previously described, the control unit 61 can also adapt the control or regulation of the oxygen concentration ($FiO_2$) on the basis of the quality of the data as a function of the quality of the determined data on the basis of presettings stored in the classification data 52. Such an adaptation, for example, in a situation with very low data quality (SQ=low), is then performed by the control unit 61 by means of setting values 43 during the control or regulation of the ventilation temporarily or permanently without taking the sensor signals 19, 19' into account. In a situation with very good data quality (SQ=high), the control unit 61 can control the ventilation by means of the setting values 43 in the closed control loop (closed loop ventilation) on the basis of the $SpO_2$ signals 19 or $etCO_2$ signals 19'.

Examples of taking the quality level (SQ) 49 into account arise as shown in Table 2.

In addition, in may be made possible to adapt the alarm generation characteristic of the ventilator or anesthesia device 5 in such a situation (SQ=high) in a combination of the ventilator or anesthesia device 5 with a certain $SpO_2$ measuring system 3, for which a release is given in the ventilator or anesthesia device 5 on the basis of the property data/classification data 52. An example of this is an adaptation of a volume alarm generation ($MV_{Low}$ alarm) of the ventilation control for open ($SpO_2$ open loop ventilation) and for closed ($SpO_2$ closed loop ventilation) control loop in case of mandatory ventilation. An $SpO_2$ measuring system 3 with a quality level of data acquisition, data processing and error correction that is suitable for a leading measurement in an open and/or closed $SpO_2$ ventilation control loop is defined as an $SPO_2$ measuring system 3 here.

If an $SpO_2$ signal detection takes place in an open control loop ($SpO_2$ open loop ventilation) with monitoring of compliance with an $SpO_2$ minimum, e.g., >92%, on the basis of the $SpO_2$ signal 19 detected with the previously defined $SpO_2$ measuring system 3, the physiological alarm required by the regulation ($MV_{Low}$ alarm), which indicates an excessively low respiratory minute volume (AMV) during the mandatory ventilation, can be signaled, for example, with a lower priority of alarm generation than a so-called "silent alarm" (muting) or delayed in time (alert delay).

Examples of the adaptation of the alarm generation characteristic appear from Table 1b.

If a regulation is carried out by means of the control unit 61 by means of setting values 43 in a control in a constellation of a closed control loop ($SpO_2$ closed loop ventilation) with regulation of the ventilation to an $SpO_2$ target value on the basis of the $SpO_2$ signal 19 detected with the above-described, defined $SpO_2$ measuring system 3, the $MV_{Low}$ alarm may be signaled, for example, with a lower priority, it may be signaled with a time delay (alert delay) or signaled as a "silent alarm" (muting). The signaling of the $MV_{Low}$ alarm may, for example, also be deactivated, in principle, in this constellation. Such an adaptation of the alarm generation characteristic is possible because in case of mandatory ventilation in the closed control loop ($SpO_2$ closed loop ventilation), the monitoring of the $SpO_2$ target value with narrow limit values, for example, 95%±2%, ensures that the patient 7 is supplied with a sufficient quantity of breathing air. The exchange of oxygen and carbon dioxide in the lungs (blood gas exchange) now leads, as is expected, to an oxygen saturation in the blood into the range of the set $SpO_2$ target value. The sufficient supply of the patient 7 with oxygen is thus ensured without the minute volume having to be monitored particularly closely in all applications.

This leads to the advantage that, in particular, alarm generations for an excessively low minute volume ($MV_{Low}$ alarm), where the corresponding alarm limit value is set in many cases very cautiously by the clinical staff, so that a certain number of $MV_{Low}$ false alarms is thus also consciously tolerated or accepted by the clinical staff, can be made more comfortable for the clinical staff in the clinical routine and care for the patient 7 in case of mandatory ventilation in the closed control loop ($SpO_2$ closed loop ventilation) concerning the $MV_{Low}$ alarm generation. These examples mentioned for the $SpO_2$ control loop on the basis of $SpO_2$ sensor signals 19 can, in principle, be extrapolated to the control or regulation of the ventilation on the basis of $etCO_2$ sensor signals 19 concerning the adaptation and setting of setting values 43 and operating parameters 43 of the ventilator or anesthesia device 5. It is thus possible, for example, that the ventilator or anesthesia device 5 carries out a weaning of the patient 7 from the mechanical ventilation on the basis of the $etCO_2$ sensor signals 19' provided by means of the $etCO_2$ measuring system in the data network via the data network 60 and sets, controls or regulates for this the pressure assist of the ventilator or anesthesia device 5 by means of the setting values 43.

Examples of the adaptation of alarm threshold values appear from Table 1c.

FIG. 2b shows a special embodiment of the medical system 1 with the measuring system 3 and with the ventilator or anesthesia device 5 according to FIG. 2a. In addition to the use of the first asymmetric encryption pair 70, which is used to identify the measuring system 3 at the ventilator or anesthesia device 5, a second asymmetric encryption pair 80 is used in FIG. 2b to encrypt the data transmission via the data network 60 within the medical system 1 between the measuring system 3 and the ventilator or anesthesia device 5. The manner of functioning in which sensor signals 19, 19' reach the first data processing unit 33 of the measuring system 3 corresponds to the data processing as it is described in connection with FIG. 2a. Identical components in FIGS. 2a and 2b are designated by the same reference numbers in FIGS. 2a and 2b. A first (measuring system) data set 39 is generated from the sensor signals 19, 19' by the first data processing unit 33 in FIG. 2b, digitized into a first (measuring system) data item 39' for the data transmission, and converted into a signed first data item 39" by means of the private key (PSM1) 73 of the first asymmetric encryption pair. An encryption of the signed first data item 39" to a signed and encrypted first data item 39'" is now additionally performed in this FIG. 2b by means of a public key (ÖSB2) 81 of the second asymmetric encryption pair 80. This encrypted and signed first data item 39'" is transmitted by means of the first data output unit 35 over the transmission channel 60 or via the data network 60 to the first data-receiving unit 57 to the ventilator or anesthesia device 5. The signed and encrypted first data item 39'" is again decrypted there by the second data processing unit 53 by means of the private key (PSB2) 83 of the second asymmetric encryption pair 80. As is described in connection with FIG. 2*a*, the first signature element 45 and the first data set 39 are again obtained in this case by means of the public key (ÖSM1) 71 of the first asymmetric encryption pair. The comparison of the signature element 45 with the classification data 52 and the subsequent configuring of setting values 43 or operating parameters 43 by the control unit 61 of the ventilator or anesthesia device 5, which configuration depends on this, takes place as was described in connection with FIG. 2*a*. This embodiment according to FIG. 2*b* thus offers the advantage that the data transmission within the medical system 1 via the data network 60 cannot be used by third parties in a simple manner, for example, by eavesdropping on the data transmission in the data network 60. This is prevented by means of the asymmetric encryption by means of the second asymmetric encryption pair 80. In embodiments in which, for example, personal data of the patient 7 shall be transmitted with the data packets of the sensor signals 19, 19' to the ventilator or anesthesia device 5 from the measuring system 3 to the ventilator or anesthesia device 5 by means of the data network 60, it may be useful and highly appropriate to encrypt the data in order to prevent a possible abuse of personal data, for example, age, clinical picture, length of hospital stay, by unauthorized persons.

Unlike FIG. 2*a*, FIG. 3*a* shows in the medical system 1 a data transmission from the ventilator or anesthesia device 5 to the measuring system 3. Identical components in FIGS. 1, 2*a*, 2*b*, 3*a* are designated by the same reference numbers. An information signal 63, which corresponds to certain states or setting values or measured values, which are obtained, detected or determined in the ventilator or anesthesia device 5, are sent to the second data processing unit 53 by the control unit 61. The information signal 63 is converted into a second data set 59 in the data processing unit 53. This conversion may be, for example, a digitization of analog data or a conversion of data formats into other data formats or a conversion or transformation of different protocols or command structures. This second data set 59 is converted in the second data output unit 55 into a data item 59' and converted into a signed second data item 59" by means of a private key (PSB2) 83 of a second asymmetric encryption pair 80. This private key (PSB2) 83 of the second asymmetric encryption pair 80 is provided by a second memory 51 of the second data processing unit 53. The signed second data item 59" is entered by the second data processing unit 53 into the data network 60 or to the transmission channel 60 by means of a second data output unit 55 and transmitted to the measuring system 3 or to the second data-receiving unit 37 thereof. The signed second data item 59" is sent to the first data processing unit 33 from the second data-receiving unit 37. A data processing is performed within the first data processing unit 33 in the form that the second data set 59 and a second signature element 65 are extracted by means of a public key (ÖSB2) 81 of the second asymmetric encryption pair 80, which public key is provided by the first memory 31. A checking is then performed to determine whether the ventilator or anesthesia device 5 belongs to a certain ventilator or anesthesia device, to a certain type of ventilator or anesthesia device or to a certain group of ventilators or anesthesia devices. Identification data 32 for different types of ventilators or anesthesia devices 5 are kept available for this checking in the first memory 31 of the measuring system and are used by the first data processing unit for the checking 67. The second data set 59 is now available to the first data processing unit 33 for configuring the functionality of the measuring system 3, for example, the manner of measured value acquisition of the sensor signals 19, 19' or the processing thereof. It is thus possible, for example, to deactivate a data filtration of the signals 19, 19' as a function of the second data set 59 if it should be necessary to transmit the sensor signals 19, 19' to the ventilator or anesthesia device unfiltered for carrying out the ventilation by the ventilator or anesthesia device in order to perform, for example, another operation, for preferably a control with other control parameters (KP, TN, TV) on the basis of the sensor signals 19, 19'.

Another possibility of using the information signals 63 for configuring the functionality of the measuring system 3 is that a special adaptation of alarm generations is made possible during the measuring operation of the measuring system 3 for certain devices and especially for ventilators or anesthesia devices, for which special information is present in the identification data 32 in the first memory 31 of the measuring system 3. For example, an alarm generation in case of an excessively low oxygen saturation in the blood of a patient 7 (SpO$_2$ Low) can thus be deactivated on the measuring system 3 or an alarm can at least be outputted as a so-called silent alarm if, as was described in detail in FIG. 2*a*, the SpO$_2$ value was transmitted from the measuring system 3 to the ventilator or anesthesia device 5 and this value is already taken into consideration at the ventilator or anesthesia device 5, for example, in an alarm generation at the ventilator or anesthesia device 5. It is possible in this manner to avoid an alarm generation for such an alarm generation situation or the same alarm generation situation simultaneously at two devices on the basis of the information signals 63. This offers the advantage that the situation for monitoring the patient 7 can be made more comfortable for the clinical staff because the alarm generations do not take place simultaneously at different devices 3, 5.

FIG. 3*b* shows an embodiment of an interaction between the ventilator or anesthesia device 5 with the measuring system 3 in a medical system according to FIG. 3*a* in a special variant. Identical components in FIGS. 1, 2*a*, 2*b*, 3*a* and 3*b* are designated by the same reference numbers in FIGS. 1, 2*a*, 2*b*, 3*a* and 3*b*. Similarly to what was described in connection with FIG. 2*b*, the information signal 63 is both signed and encrypted in FIG. 3*b* and is transmitted as an encrypted second data item 59''' to the transmission channel 60 or via the data network 60 to the measuring system 3. This is carried out in the following manner. The information signal 63, which contains or indicates information of the ventilator or anesthesia device 5 in the ventilator or anesthesia device, as was described in connection with FIG. 3*a*, is provided by the control unit 61 as a second (ventilator/anesthesia device) data set 59 for the second data processing unit 53 as a second (ventilator/anesthesia device) data item 59'. The second data item 59' is signed by means of the private key 83 of the second asymmetric encryption pair 80 to form a second (ventilator/anesthesia device) signed data item 59". An encryption is subsequently performed by means of a public key 71 of the first asymmetric encryption pair 70, which public key is provided by the second memory 51. A second (ventilator/anesthesia device) signed and encrypted data item 59''' is then available, which is provided for the second data-receiving unit 37 at the measuring system 3 via the second data output unit 55. Decryption of the second signed and encrypted data item 59''' is performed in the measuring system 3 by means of the private key (PSM1) 73 of the first asymmetric encryption pair 70, which private key is stored in the first memory 31. The further processing of the second data set 59 available after the decryption with checking 67 on the basis of identification data 32 takes place as described before in connection with FIG. 3*a*. It can be ensured by the encryption of the information signal 61 of the ventilator or anesthesia device 5 on the way over the data network 60 to the measuring system 3 that the adaptation of the alarm generation described above as an example in connection with FIG. 3*a* with the aforementioned silent alarm or with the alarm deactivation is not enabled by an access to the data network 60 from the outside by means of a manipulation. Just as the identification, the encryptions are thus used to increase the functional reliability in the interaction of the ventilator or anesthesia device 5 with the measuring system 3 in the medical system 1.

It is seen, as a result, that both an unambiguous assignment of measuring systems 3, especially certain measuring systems 3, to a ventilator or anesthesia device 5, and securing of the transmission of the data transmitted between these two interacting devices 3, 5 are made possible by the use of asymmetric encryption pairs 70, 80 (FIG. 2*a*, FIG. 2*b*, FIG. 3*a*, FIG. 3*b*).

While specific embodiments of the invention have been shown and described in detail to illustrate the application of the principles of the invention, it will be understood that the invention may be embodied otherwise without departing from such principles.

APPENDIX

List of Reference Numbers

1 Medical system
3 Measuring system (M1)
5 Ventilator or anesthesia device (B2)
7 Patient/living being
9 Ventilation tube system with sampling tube
11 Sensor for measuring an oxygen saturation in the blood of the patient 7
13 Sensor for detecting a carbon dioxide concentration in the breathing gas of the patient 7
15 Sensor module
17 Interface
19, 19' Sensor signals
31 Measuring system memory
32 Identification data
33 Measuring system data processing unit
35 Measuring system data output unit
37 Measuring system data-receiving unit
39 Measuring system data set
39' Measuring system data item
39" Measuring system data item, signed
39''' Measuring system data item, signed and encrypted
43 Setting value/operating parameter
45 First (measuring system) signature element (SEM1)
47 First (measuring system) checking result
49 Quality level (SQ)
51 Ventilator/anesthesia device memory
52 Classification data
53 Ventilator/anesthesia device data processing unit
55 Ventilator/anesthesia device data output unit
57 Ventilator/anesthesia device data-receiving unit
59 Ventilator/anesthesia device data set
59' Ventilator/anesthesia device data item
59" Ventilator/anesthesia device data item, signed
59''' Ventilator/anesthesia device data item, signed and encrypted
60 Transmission channel, data network
60' Components in the data network, transmission channel
60" Data transmission protocol (TCP/IP)
61 Control unit
63 Information signal
65 Second (ventilator/anesthesia device) signature element (SEB2)
67 Second (ventilator/anesthesia device) checking result
70 First (measuring system) asymmetric encryption pair
71 Public key (ÖSM1) of the first (measuring system) asymmetric encryption pair
73 Private key (PSM1) of the first (measuring system) asymmetric encryption pair
80 Second (ventilator/anesthesia device) asymmetric encryption pair
81 Public key of the second (ventilator/anesthesia device) asymmetric encryption pair (ÖSB2)
83 Private key (PSB2) of the second (ventilator/anesthesia device) asymmetric encryption pair

What is claimed is:

1. A medical system for providing and exchanging data, the medical system comprising:
a data network with a transmission channel;
a measuring system comprising:
a sensor module interface configured to detect at least one sensor signal provided by a sensor module, wherein a physiological parameter of a living being is indicated by the at least one sensor signal;
a measuring system memory;
a measuring system data output unit configured to generate at least one measuring system data set based on the at least one sensor signal; and
a measuring system data processing unit configured to sign a measuring system data item derived from the at least one measuring system data set with a private key of a measuring system asymmetric encryption pair, which private key is assigned to the measuring system and is provided by the measuring system memory, wherein the measuring system data output unit is configured to provide the signed measuring system data item to the transmission channel; and
a ventilator or anesthesia device comprising:
a ventilator/anesthesia device data-receiving unit configured to receive the signed measuring system data item from the transmission channel;
a ventilator/anesthesia device memory, wherein a public key of the measuring system asymmetric encryption pair is stored in the ventilator/anesthesia device memory and is assigned to the measuring system;
a ventilator/anesthesia device processing unit, wherein the ventilator/anesthesia device data-receiving unit or the ventilator/anesthesia device processing unit is configured to extract a measuring system signature element from the received measuring system data item and the ventilator/anesthesia device processing unit is further configured to check, based on the public key of the measuring system asymmetric encryption pair stored in ventilator/anesthesia device memory and further based on the at least one measuring system data set extracted from the measuring system data item and the measuring system signature element, whether the measuring system signature element corresponds to the public key wherein the ventilator/anesthesia device processing unit is further configured to check, based on the measuring system signature element and based on additional classification data provided by the ventilator/anesthesia device memory, whether the sensor module belongs to a certain sensor module or to a certain class of measuring systems; and a control unit is configured to control or influence a ventilation based on at the at least one sensor signal, contained in the at least one measuring system data set, as a function of a checking result of checking (i) at least one setting value, or (ii) an operating parameter, or (iii) both at least one setting value and an operating parameter, of the ventilator or anesthesia device, wherein the control unit is configured, as a function of the checking result, (i) to adapt an alarm organization, or (ii) to adapt executing an alarm organization, or (iii) both to adapt an alarm organization and to adapt executing the alarm organization, during the operation of the ventilator or anesthesia device, wherein the control unit is configured, as a function of the checking result, to adapt physiological alarm threshold values during the control of the ventilation during the operation of the ventilator or anesthesia device based on the at least one sensor signal.

2. A medical system in accordance with claim 1, wherein: the interface or the measuring system data processing unit are configured to determine a quality level based on the sensor signal and to provide the quality level in the at least one measuring system data set; and the control unit is configured, as a function of the checking result or based on the quality level provided in the at least one measuring system data set or as a function of both the checking result and based on the quality level provided in the at least one measuring system data set, to control or influence the at least one setting value or the operating parameter of the ventilator or anesthesia device used for carrying out the ventilation or to control or influence both the at least one setting value and the operating parameter of the ventilator or anesthesia device used for carrying out the ventilation.

3. A medical system in accordance with claim 1, wherein: the ventilator or anesthesia device further comprises a ventilator/anesthesia device data output unit provided in or at the ventilator or anesthesia device;

the ventilator/anesthesia device processing unit is configured to generate at least one ventilator/anesthesia device data set based on at least one information signal provided by the ventilator or anesthesia device;

a type of the ventilator or anesthesia device or a state of the ventilator or anesthesia device or a current mode of operation of the ventilator or anesthesia device or any combination of a type of the ventilator or anesthesia device, a state of the ventilator or anesthesia device, and a current mode of operation of the ventilator or anesthesia device is indicated by the at least one information signal;

the ventilator/anesthesia device processing unit is configured to sign a ventilator/anesthesia device data item derived from the at least one ventilator/anesthesia device data set with a private key of a ventilator/anesthesia device asymmetric encryption pair, which private key is provided by the ventilator/anesthesia device memory;

the ventilator/anesthesia device data output unit is configured to provide the signed ventilator/anesthesia device data item to the transmission channel;

the measuring system further comprises a measuring system data-receiving unit configured to receive the at least one signed ventilator/anesthesia device data item of the ventilator or anesthesia device in or at the measuring system;

the measuring system data-receiving unit or the measuring system data processing unit is configured to extract a signature element from the at least one ventilator/anesthesia device data item received;

the measuring system data processing unit is further configured to check based on a public key of the ventilator/anesthesia device asymmetric encryption pair, which public key is assigned to the ventilator or anesthesia device, and further based on the at least one ventilator/anesthesia device data set extracted from the ventilator/anesthesia device data item and based on the ventilator/anesthesia device signature element, whether the ventilator/anesthesia device signature element is configured corresponding to the public key;

the measuring system data processing unit is configured to check, based on the ventilator/anesthesia device signature element and based on identification data provided by the measuring system memory, whether the ventilator or anesthesia device is identical to a certain ventilator or anesthesia device;

the measuring system data processing unit or the interface is configured to provide a another checking result of the checking; and the measuring system data processing unit or the interface is configured, as a function of the another checking result, to:

adapt a signal detection of the sensor signal during the generation of at least one measuring system data set; or adapt a signal processing of the sensor signal during the generation of at least one measuring system data set; or adapt both a signal detection and a signal processing of the sensor signal during the generation of at least one measuring system data set; or adapt alarm threshold values during execution of an alarm organization; or adapt alarm threshold values during execution of the alarm organization during the operation of the sensor module; or adapt alarm threshold values during execution of an alarm organization and adapt alarm threshold values during execution of the alarm organization during the operation of the sensor module.

4. A medical system in accordance with claim 3, wherein: the ventilator/anesthesia device processing unit is configured to encrypt the ventilator/anesthesia device data item with the public key of the measuring system asymmetric encryption pair, which public key of the measuring system asymmetric encryption pair is assigned to the measuring system;

the ventilator/anesthesia device data output unit is configured to provide the encrypted, signed ventilator/anesthesia device data item to the transmission channel; and the measuring system data-receiving unit or the measuring system data processing unit is configured to decrypt the signed and encrypted ventilator/anesthesia device data item received from the transmission channel with the private key of the measuring system asymmetric encryption pair, which private key of the of the measuring system asymmetric encryption pair is provided by the ventilator/anesthesia device memory, and to provide the decrypted ventilator/anesthesia device data item as the at least one ventilator/anesthesia device data set to the measuring system data processing unit or for the interface.

5. A medical system in accordance with claim 3, wherein the transmission channel comprises at least one component configured to store or temporarily store signals, data and/or information, for a data distribution and data organization as well as for the organization of the data exchange in the data network between the measuring system and the ventilator or anesthesia device.

6. A medical system in accordance with claim 5, wherein the identification data are provided for the measuring system memory by the transmission channel and by the at least one component.

7. A medical system in accordance with claim 1, wherein the checking result of the checking carried out to determine whether the sensor module belongs to a certain measuring system or sensor module or to a certain class of measuring systems or sensor modules is indicated by at least one information signal.

8. A medical system in accordance with claim 7, wherein:
the ventilator/anesthesia device processing unit is configured to encrypt the ventilator/anesthesia device data item with the public key of the measuring system asymmetric encryption pair, which public key of the measuring system asymmetric encryption pair is assigned to the measuring system;
the ventilator/anesthesia device data output unit is configured to provide the encrypted, signed ventilator/anesthesia device data item to the transmission channel; and
the measuring system data-receiving unit or the measuring system data processing unit is configured to decrypt the signed and encrypted ventilator/anesthesia device data item received from the transmission channel with the private key of the measuring system asymmetric encryption pair, which private key of the of the measuring system asymmetric encryption pair is provided by the ventilator/anesthesia device memory, and to provide the decrypted ventilator/anesthesia device data item as the at least one ventilator/anesthesia device data set to the measuring system data processing unit or for the interface.

9. A medical system in accordance with claim 1, wherein:
the measuring system data processing unit is configured to sign and encrypt the measuring system data item with the public key of the ventilator/anesthesia device asymmetric encryption pair;
the public key of the ventilator/anesthesia device asymmetric encryption pair is assigned to the ventilator or anesthesia device;
the measuring system data output unit is configured to provide the encrypted, signed measuring system data item to the transmission channel; and
the ventilator/anesthesia device data-receiving unit is configured to decrypt the received, signed and encrypted measuring system data item with the private key of the ventilator/anesthesia device asymmetric encryption pair, which private key of the ventilator/anesthesia device asymmetric encryption pair is provided by the measuring system memory, and to provide the decrypted measuring system data item as at least one measuring system data set for the control unit.

10. A medical system in accordance with claim 9, wherein:
the ventilator/anesthesia device processing unit is configured to encrypt the ventilator/anesthesia device data item with the public key of the measuring system asymmetric encryption pair, which public key of the measuring system asymmetric encryption pair is assigned to the measuring system;

the ventilator/anesthesia device data output unit is configured to provide the encrypted, signed ventilator/anesthesia device data item to the transmission channel; and
the measuring system data-receiving unit or the measuring system data processing unit is configured to decrypt the signed and encrypted ventilator/anesthesia device data item received from the transmission channel with the private key of the measuring system asymmetric encryption pair, which private key of the of the measuring system asymmetric encryption pair is provided by the ventilator/anesthesia device memory, and to provide the decrypted ventilator/anesthesia device data item as the at least one ventilator/anesthesia device data set to the measuring system data processing unit or for the interface.

11. A medical system in accordance with claim 1, wherein the transmission channel comprises at least one component configured to store or temporarily store signals, data and/or information, for a data distribution and data organization as well as for the organization of the data exchange in the data network between the measuring system and the ventilator or anesthesia device.

12. A medical system in accordance with claim 11, wherein data are provided and exchanged in the data network with the Transmission Control Protocol (TCP, Transport Layer) and Internet Protocol (IP, Network Layer) network data transmission protocol (TCP/IP).

13. A medical system in accordance with claim 11, wherein the classification data is provided for the ventilator/anesthesia device memory by the transmission channel and by the at least one component.

14. A medical system for providing and exchanging data, the medical system comprising:
a data network with a transmission channel;
a measuring system comprising:
a sensor module interface configured to detect at least one sensor signal provided by a sensor module, wherein a physiological parameter of a living being is indicated by the at least one sensor signal;
a measuring system memory;
a measuring system data output unit configured to generate at least one measuring system data set based on the at least one sensor signal; and
a measuring system data processing unit configured to sign a measuring system data item derived from the at least one measuring system data set with a private key of a measuring system asymmetric encryption pair, which private key is assigned to the measuring system and is provided by the measuring system memory, wherein the measuring system data output unit is configured to provide the signed measuring system data item to the transmission channel; and
a ventilator or anesthesia device comprising:
a ventilator/anesthesia device data-receiving unit configured to receive the signed measuring system data item from the transmission channel;
a ventilator/anesthesia device memory, wherein a public key of the measuring system asymmetric encryption pair is stored in the ventilator/anesthesia device memory and is assigned to the measuring system;
a ventilator/anesthesia device processing unit, wherein the ventilator/anesthesia device data-receiving unit or the ventilator/anesthesia device processing unit is configured to extract a measuring system signature element from the received measuring system data item and the ventilator/anesthesia device processing unit is further configured to provide a determination output, the determination output comprising a determination as to whether the measuring system signature element corresponds to the public key based on the public key of the measuring system asymmetric encryption pair stored in ventilator/anesthesia device memory and further based on the at least one measuring system data set extracted from the measuring system data item and the measuring system signature element, the determination output further comprising a determination as to whether the sensor module belongs to a certain sensor module or to a certain class of measuring systems based on the measuring system signature element and based on additional classification data provided by the ventilator/anesthesia device memory; and a control unit receiving the determination output as input and the control unit controlling ventilation of a patient based on the determination output, wherein the control unit is configured, based on the determination output, (i) to adapt an alarm organization, or (ii) to adapt executing an alarm organization, or (iii) both to adapt an alarm organization and to adapt executing the alarm organization, during the operation of the ventilator or anesthesia device, wherein the control unit is configured, based on the determination output, to adapt physiological alarm threshold values during the control of the ventilation during the operation of the ventilator or anesthesia device based on the at least one sensor signal.

15. A medical system in accordance with claim 14, wherein:

the interface or the measuring system data processing unit are configured to determine a quality level based on the sensor signal and to provide the quality level in the at least one measuring system data set; and the control unit is configured, based on one or more of determination output and the quality level provided in the at least one measuring system data set, to control or influence the at least one setting value or the operating parameter of the ventilator or anesthesia device used for carrying out the ventilation or to control or influence both the at least one setting value and the operating parameter of the ventilator or anesthesia device used for carrying out the ventilation.

16. A medical system in accordance with claim 14, wherein the transmission channel comprises at least one component configured to store or temporarily store signals, data and/or information, for a data distribution and data organization as well as for the organization of the data exchange in the data network between the measuring system and the ventilator or anesthesia device.

17. A medical system in accordance with claim 16, wherein the identification data are provided for the measuring system memory by the transmission channel and by the at least one component.

18. A medical system in accordance with claim 14, wherein the checking result of the checking carried out to determine whether the sensor module belongs to a certain measuring system or sensor module or to a certain class of measuring systems or sensor modules is indicated by at least one information signal.

* * * * *